US007111286B2

(12) United States Patent
Schrader et al.

(10) Patent No.: US 7,111,286 B2
(45) Date of Patent: Sep. 19, 2006

(54) METHOD, SYSTEM AND COMPUTER PRODUCT FOR PARSING BINARY DATA

(75) Inventors: Stuart Lyle Schrader, Brooklyn Park, MN (US); Robert J. Laferriere, Wauwatosa, WI (US); James Steven Cincotta, New Berlin, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 623 days.

(21) Appl. No.: 10/248,097

(22) Filed: Dec. 18, 2002

(65) Prior Publication Data

US 2004/0123277 A1    Jun. 24, 2004

(51) Int. Cl.
*G06F 9/44* (2006.01)
(52) U.S. Cl. .................. 717/143; 717/142; 717/144
(58) Field of Classification Search ......... 717/124–161
See application file for complete search history.

(56) References Cited

U.S. PATENT DOCUMENTS

| 4,787,035 | A | * | 11/1988 | Bourne ........................ 700/247 |
| 5,671,416 | A | * | 9/1997 | Elson ........................... 717/106 |
| 6,102,969 | A | * | 8/2000 | Christianson et al. ....... 717/146 |
| 6,353,925 | B1 | * | 3/2002 | Stata et al. ................... 717/112 |
| 6,389,425 | B1 | | 5/2002 | DeMichiel et al. ......... 707/102 |
| 6,446,256 | B1 | * | 9/2002 | Hyman et al. ............... 717/143 |
| 6,611,844 | B1 | * | 8/2003 | Saulpaugh et al. ......... 707/100 |

FOREIGN PATENT DOCUMENTS

| EP | 0 998 089 A2 | 5/1999 |
| GB | 2 385 158 A | 8/2003 |

OTHER PUBLICATIONS

GB Search Report under Section 17 (Apr. 29, 2004).

* cited by examiner

*Primary Examiner*—Tuan Dam
*Assistant Examiner*—Chuck Kendall
(74) *Attorney, Agent, or Firm*—Cantor Colburn LLP

(57) ABSTRACT

A method for parsing binary data is disclosed. The method includes receiving binary data and a parse request, the parse request calling for either a non-differenced parsing method or a differenced parsing method, invoking a parse tree and receiving a parse definition to parse the received binary data, parsing the binary data to define a value in accordance with the parse definition and calling a data builder to manage the value parsed. The value parsed is inserted into an updated data tree and an object is returned to the parse requestor.

23 Claims, 6 Drawing Sheets

Initialization

FIG. 6

Runtime

```xml
<?xml version="1.0"?>
<!DOCTYPE TrendParser [
<!ENTITY DATA_TREND_MENU SYSTEM "Data_trend_menu_def.xml">
<!ENTITY NET_ETFTP_REQ SYSTEM "../etftp/NET_ETFTP_req_def.xml">
<!ENTITY TREND_ENTRY SYSTEM "Trend_entry_def.xml">
]>
<ETFTPParser>
    &NET_ETFTP_REQ;
    &DATA_TREND_MENU;
    <Group catagory="TrendEntry">
       <Repeat count="ETFTPParser.DataTrendMenu.numberOfTrends">
       &TREND_ENTRY;
       </Repeat>
    </Group>
</ETFTPParser>
```

FIG. 10

```xml
<?xml version="1.0" ?>
<ETFTPParser>
    <Group catagory="ETFTPRequest">
        <Short name="event_id" />
        <Short name="destination_port" />

<String name="origin_loc_name" length="32" stopAtNull="true" />
    </Group>
    <Group name="DataTrendMenu" catagory="DataTrendMenu">
        <Integer name="first_storage time" />
        <Byte skip="2" />
        <Short name="numberOfTrends" switchable="true" skipSet="true" />
    </Group>
    <Group catagory="TrendEntry">
        <Repeat count="ETFTPParser.DataTrendMenu.numberOfTrends">
            <Byte name="parcode" />
            <Byte name="subcode" />
            <Byte name="slot_id" />
            <Byte name="storage_units" />
            <Byte name="display_units" />
            <Byte name="decimal_shift" signed="true" />
        </Repeat>
    </Group>
</ETFTPParser>
```

METHOD, SYSTEM AND COMPUTER PRODUCT FOR PARSING BINARY DATA

BACKGROUND OF INVENTION

The present disclosure relates generally to a method for parsing data, and particularly to a method of parsing binary data.

Hospitals typically utilize computer systems to manage the various departments within the hospital. Data about each patient is collected by a variety of computer systems. For example, a patient may be admitted to the hospital for the monitoring of vital signs. Information about the patient (e.g., demographics and insurance) could be obtained by the hospital information system (HIS) and stored on a patient record. This information could then be passed to a particular department information system (DIS). Typically the DIS is a product of one company, while the HIS is the product of another company. As a result, the databases between the two will differ. Further, they will capture/retain and send different levels of granularity in the data. Once the patient information has been received by the DIS, the patient can be scheduled for a parametric study (a parameter of the parametric study is a grouping of vital signs). Next, the parametric study is performed by a clinician. Images and measurements are taken and sent to the DIS server. The reading physician (e.g., a medical specialist) sits down at a review station and pulls the patient's parametric study. The medical specialist then begins to review the images and measurements and creates a complete medical report on the study. The medical report can then be coded as a structured report (SR) document including clinical data codes describing the contents of the report. When the medical specialist completes the medical report, the report is sent to the DIS server where it is stored and associated with the patient through patient identification data. The completed medical report with clinical data codes is one example of the kind of report that could be sent over a network to a data repository as a binary data stream.

Typically, these binary data structures contain data values that define how to interpret binary sub-structures that follow in the data stream. In turn, those binary sub-structures may contain additional type fields that define further sub-structures within them. As the process continues, forming a hierarchal set of structures, a large and complex data structure can evolve, resulting in slow data transmission over low bandwidth communication lines.

SUMMARY OF INVENTION

In one embodiment, a method for parsing binary data includes receiving binary data and a parse request, the parse request calling for either a non-differenced parsing method or a differenced parsing method, invoking a parse tree and receiving a parse definition to parse the binary data, parsing the binary data to define a value in accordance with the parse definition, calling a data builder to manage the value parsed, inserting the value into a data tree, and returning an object to the parse requestor.

In another embodiment, a method for parsing medical binary data for transmission over a communication line includes receiving binary data and a parse request, the parse request calling for either a non-differenced parsing method or a differenced parsing method, storing a last known data tree in a memory, invoking a parse tree and receiving a parse definition to parse the binary data, parsing the binary data to define a value in accordance with the parse definition, calling a data builder to manage the value parsed, inserting the value into an updated data tree, retrieving the last known data tree from memory if a differenced parsing method was called, comparing the updated data tree to the last known data tree if a differenced parsing method was called, creating a differenced tree containing the changes from the last known data tree to the updated data tree if a differenced parsing method was called, and returning either the updated data tree or the differenced tree to the parse requestor.

In a further embodiment, a system for parsing binary data includes a hospital computer system having software to implement a method for parsing medical binary data for transmission over a communication line. The hospital computer system being in communication with a network, and the software including instructions for receiving binary data and a parse request, the parse request calling for either a non-differenced parsing method or a differenced parsing method, storing a last known data tree in a memory, invoking a parse tree and receiving a parse definition to parse the binary data, parsing the binary data to define a value in accordance with the parse definition and calling a data builder to manage the value parsed, inserting the value into an updated data tree, retrieving the last known data tree from memory if a differenced parsing method was called, comparing the updated data tree to the last known data tree if a differenced parsing method was called, creating a differenced tree containing the changes from the last known data tree to the updated data tree if differenced parsing method was called, and returning either the updated data tree or the differenced tree to the parse requestor.

In another embodiment, a method for parsing binary data includes initializing a value parser by reading a parse definition file and creating a parse tree representative of the parse definition, accepting binary data input having either a primitive data element or a non-primitive data element, calling a data builder in response to the primitive data element and inserting the primitive data element into a data tree at a primitive parse node, calling a data builder in response to the non-primitive data element and inserting the non-primitive data element into the data tree at a non-primitive parse node, and establishing and returning either a non-differenced data tree or a differenced tree.

In a further embodiment, a computer program product for parsing binary data includes a storage medium, readable by a processing circuit, storing instructions for execution by the processing circuit for receiving binary data and a parse request, the parse request calling for either a non-differenced parsing method or a differenced parsing method, storing a last known data tree in a memory, invoking a parse tree receiving a parse definition to parse the received binary data, parsing the binary data to define a value in accordance with the parse definition and calling a data builder to manage the value parsed, inserting the value into an updated data tree, retrieving the last known data tree from the memory if a differenced parsing method was called, comparing the updated data tree to the last known data tree if a differenced parsing method was called, creating a differenced tree containing the changes from the last known data tree to the updated data tree if a differenced parsing method was called, and returning either the updated data tree or the differenced tree to the parse requestor.

BRIEF DESCRIPTION OF DRAWINGS

Referring to the exemplary drawings wherein like elements are numbered alike in the several figures.

DETAILED DESCRIPTION

Figure 1:
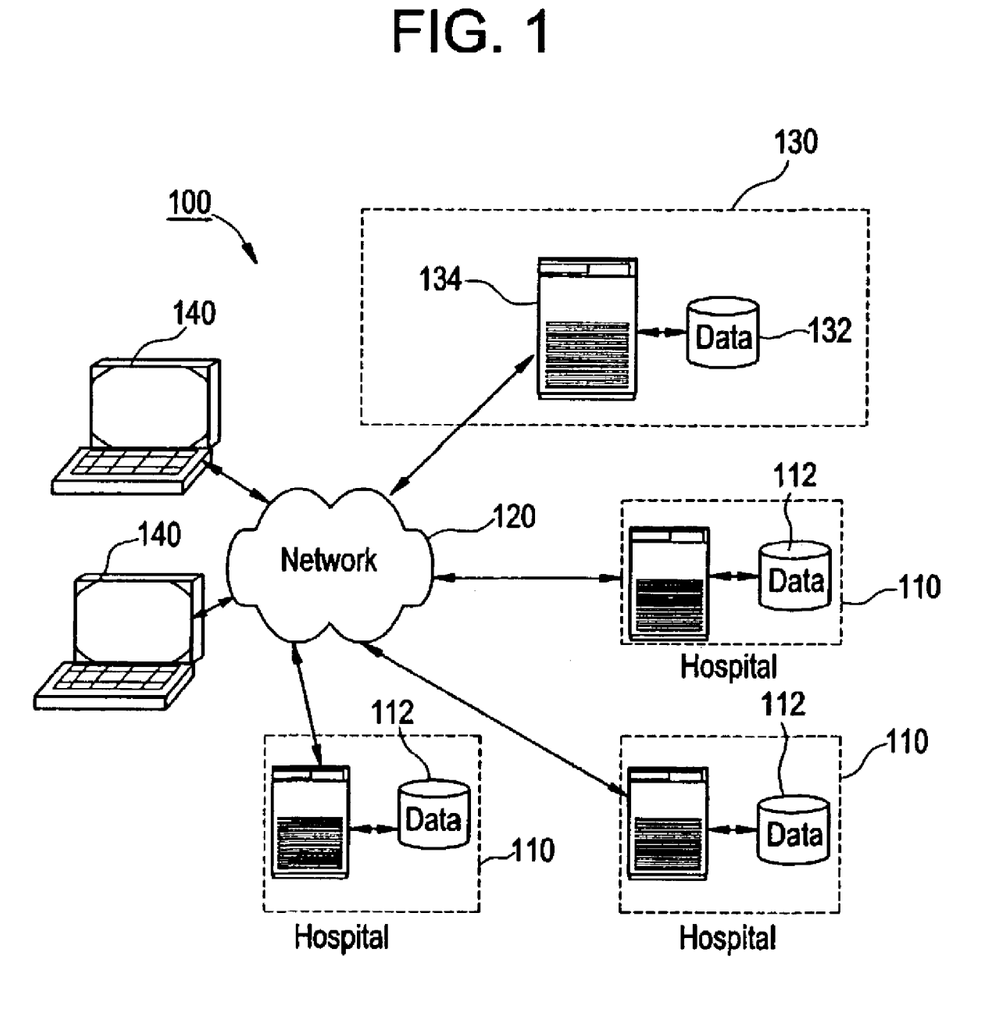
FIG. 1 is an exemplary system for parsing medical binary data.

An embodiment of the invention provides an infrastructure and process for parsing medical binary data structures, which are used for communicating raw data associated with a patient or updating medical device interfaces and drivers over a computer network. FIG. 1 is an exemplary system for parsing medical binary data. Hospital computer systems 110 located at various hospitals are connected to a network 120. The hospital computer systems 110 send medical data to a host system 130 that includes a data repository located on a host storage device 132 and a host computer 134. The hospital computer systems 110 typically include application software to perform coded medical reporting and network interfacing along with one or more hospital storage devices 112 for storing the coded medical data. In addition, the hospital computer systems 110 include application software to parse the medical data, arranged as binary data structures, into a suitable format for ease of transmission over communication lines, and to do so without including protocol information embedded within the data stream, thereby enabling compressed communication over existing communication lines, which may have a low bandwidth, without the need for line upgrades. The parsed data objects, including parse trees and data trees, are stored on host storage device 132 for access across multiple hospital computer systems 110.

Figure 3:
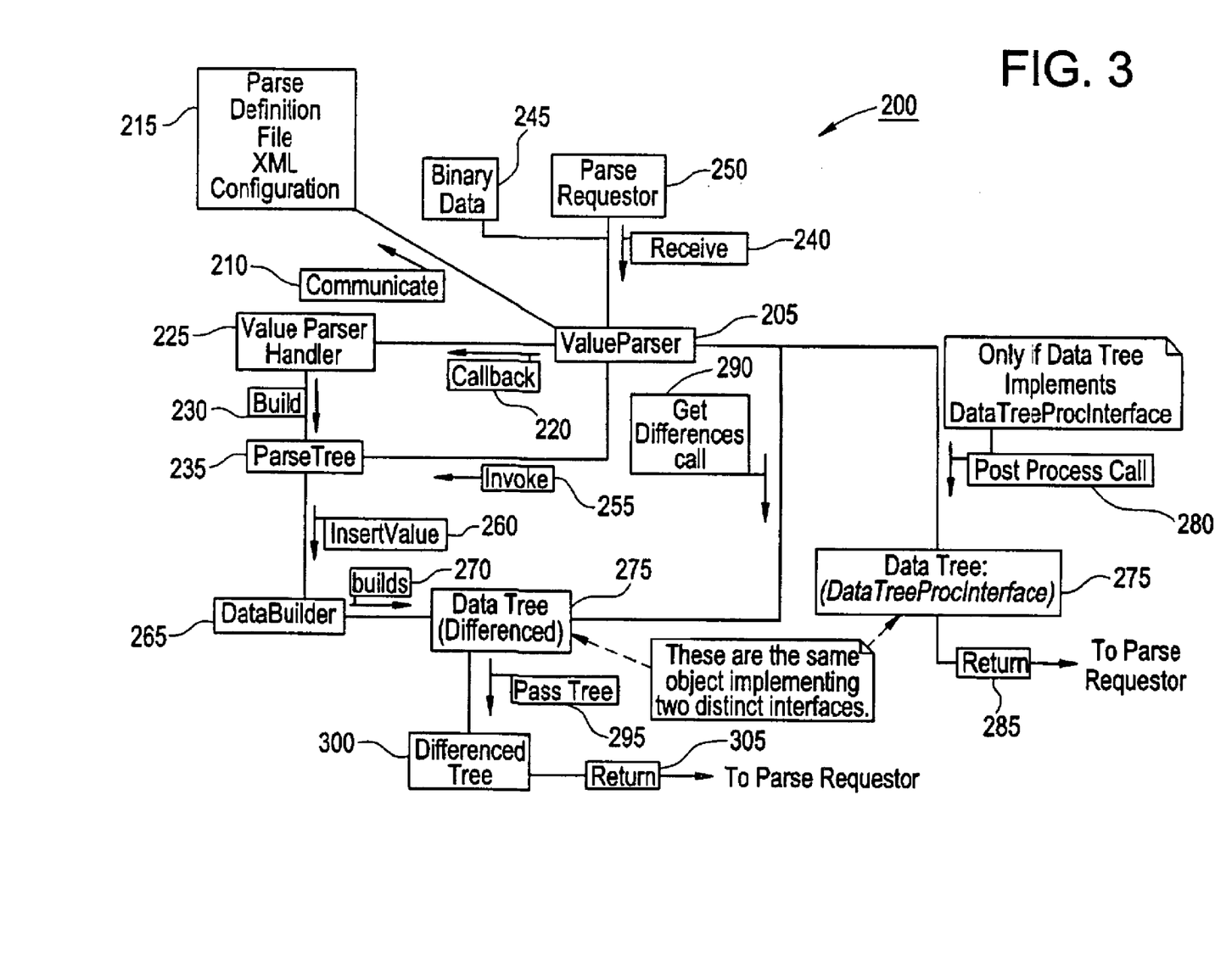
FIG. 3 is an exemplary process block diagram for parsing medical binary data on the system of FIG. 1.

In general, a parse tree is an information tree that represents the structure of the binary data being read in and contains a hierarchy of parse nodes (branches and leaves of the tree). The parse tree is stored by a value parser and called repeatedly at runtime as binary data is received. A data tree is an information tree that represents the parsed data values of the received binary data in a hierarchal form suitable for processing by a program. A data builder is a class of software that builds the data tree and defines the format that the data tree will have. FIG. 3, described below, depicts an exemplary method for parsing medical binary data.

The system 100 of FIG. 1 includes one or more user systems 140 through which an end-user, or customer, can make a request to an application program on the host computer 134 to access particular information stored in the data repository located on the host storage device 132. In an exemplary embodiment, the host computer 134 executes programs that provide access to data contained in the data repository located on the storage device 132. The user systems 140 can be directly connected to the host computer 134 or they could be coupled to the host computer 134 via the network 120. Each user system 140 may be implemented using a general-purpose computer executing a computer program for carrying out the processes described herein. The user systems 140 may be personal computers or host attached terminals. If the user systems 140 are personal computers, the processing described herein may be shared by a user system 140 and the host computer 134 by providing an applet to the user system 140.

The network 120 may be any type of known network including a local area network (LAN), a wide area network (WAN), an intranet, or a global network (e.g., Internet). A user system 140 may be coupled to the host computer 134 through multiple networks (e.g., intranet and Internet) so that not all user systems 140 are required to be coupled to the host computer 134 through the same network. One or more of the user systems 140 and the host computer 134 may be connected to the network 120 in a wireless fashion and the network 120 may be a wireless network. In an exemplary embodiment, the network 120 is the Internet and each user system 140 executes a user interface application to directly connect to the host computer 134. In another embodiment, a user system 140 may execute a web browser to contact the host computer 134 through the network 120. Alternatively, a user system 140 may be implemented using a device programmed primarily for accessing the network 120.

The host computer 134 may be implemented using a server operating in response to a computer program stored in a storage medium accessible by the server. The host computer 134 may operate as a network server (often referred to as a web server) to communicate with the user systems 140. The host computer 134 handles sending and receiving information to and from user systems 140 and hospital computer systems 110 and can perform associated tasks. The host computer 134 may also include a firewall to prevent unauthorized access to the host computer 134 and enforce any limitations on authorized access. For instance, an administrator may have access to the entire system and have authority to modify portions of the system and a customer may only have access to view a subset of the data repository records for particular products. In an exemplary embodiment, the administrator has the ability to add new users, delete users and edit user privileges. The firewall may be implemented using conventional hardware and/or software as is known in the art.

The host computer 134 also operates as an application server. The host computer 134 executes one or more application programs to provide access to the data repository located on a host storage device 132, as well as application programs to parse medical binary data and to build parse trees and data trees for efficient communication of medical information. Processing may be shared by the user system 140 and the host computer 134 by providing an application (e.g., java applet) to the user system 140. Alternatively, the user system 140 can include a stand-alone software application for performing a portion of the processing described herein. Similarly, processing may be shared by the hospital computer systems 110 and the host computer 134 by providing an application to the hospital computer systems 110 and alternatively, the hospital computer systems 110 can include a stand-alone software application for performing a portion of the processing described herein. It is understood that separate servers may be used to implement the network server functions and the application server functions. Alternatively, the network server, firewall and the application server can be implemented by a single server executing computer programs to perform the requisite functions.

The host storage device 132 may be implemented using a variety of devices for storing electronic information such as a file transfer protocol (FTP) server. It is understood that the host storage device 132 may be implemented using memory contained in the host computer 134 or it may be a separate physical device. The host storage device 132 contains a variety of information including a data repository containing medical reports from one or more hospitals in a common format (e.g., using the same clinical codes) and a schema describing the common format and database layout. The host computer 134 may also operate as a database server and coordinate access to application data including data stored on the host storage device 132. The data repository can be physically stored as a single database with access restricted based on user characteristics or it can be physically stored in a variety of databases including portions of the database on the user systems 140 or the host computer 134. In an exemplary embodiment, the data repository is implemented using a relational database system and the database system provides different views of the data to different customers based on customer characteristics.

In an exemplary embodiment of the invention, medical data coded using different knowledge bases is transformed to a common/canonical representation. Hospitals clinicians use tools for generating clinical reports that depict an outcome of a visit by a patient. These tools use clinical codes to represent clinical terminology and the clinical codes can differ from one tool to another and from one hospital to another. In addition, the type of structured reporting (SR) object used to store the clinical data may differ from one tool to another and from one hospital to another. An exemplary embodiment of the invention can be utilized to parse changed clinical reports into a compressed representation (e.g., updated vital signs associated with a particular patient). This can provide the ability to quickly transmit updated patient data to different clinics and hospitals over a transmission line for timely use by customers such as clinicians and doctors.

Figure 2:
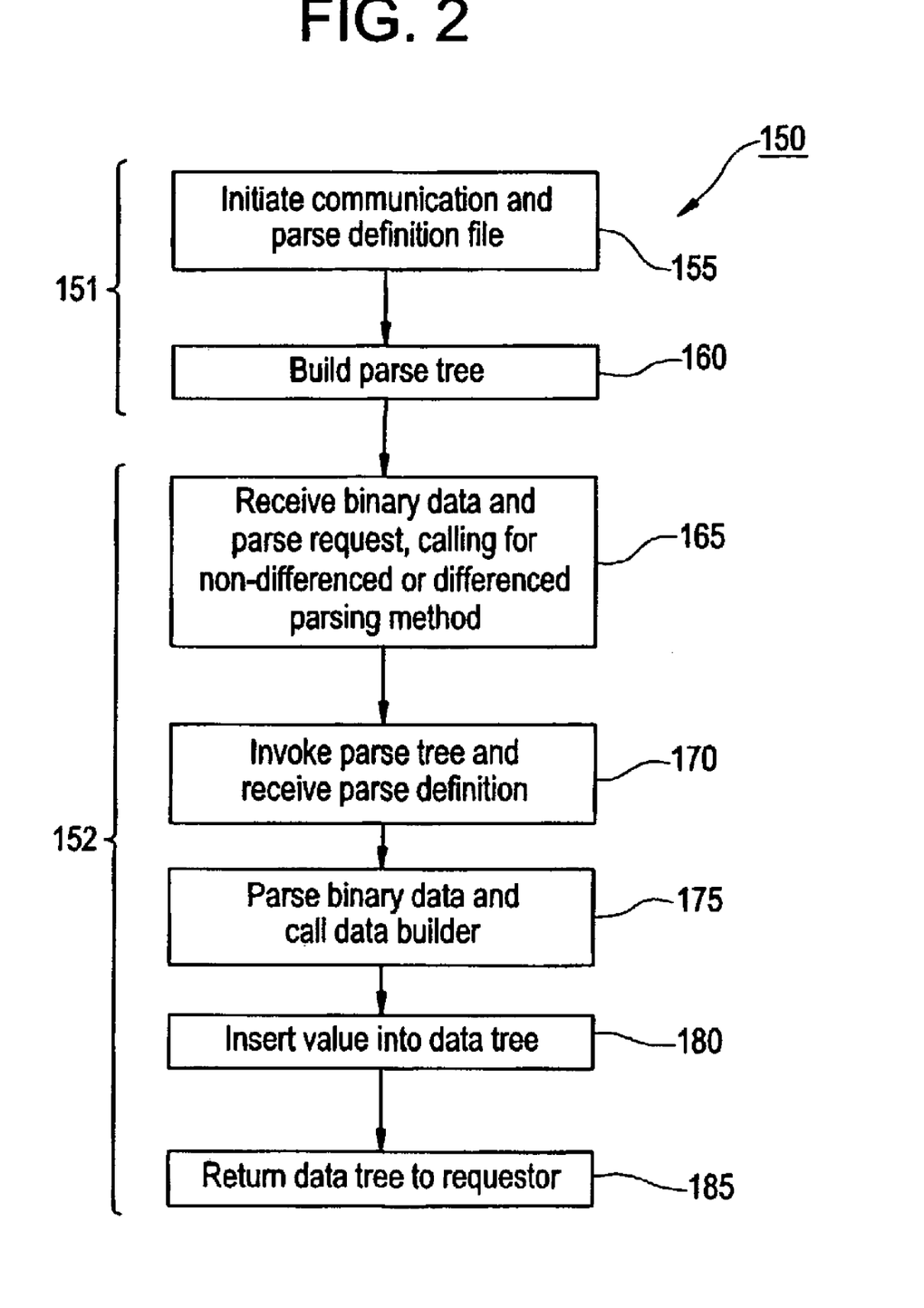
FIG. 2 is an exemplary process flowchart for parsing medical binary data on the system of FIG. 1.

Referring now to FIG. 2, a general process flowchart of an exemplary process 150 for parsing binary data that includes initialization 151 and runtime 152 phases is depicted. FIG. 3, discussed below, depicts process 150 in a more detailed block diagram form.

Beginning at block 155, process 150 initiates communication between a value parser and a parse definition file, the value parser being where the parse definition file is parsed.

At block 160, the parse tree is built at a value parser handler, which is discussed in more detail below in reference to FIG. 4.

At block 165, binary data and a parse request is received at the value parser, the parse request calling for either a non-differenced parsing method or a differenced parsing method.

At block 170, a parse tree is invoked and a parse definition is received in preparation for parsing the binary data.

At block 175, the binary data is parsed at the parse tree, thereby defining a value in accordance with the parse definition. A data builder is called to manage the parsed value and to build a data tree.

At block 180, the parsed value is inserted into the data tree, thereby updating the data tree.

At block 185, an object, such as an updated data tree or a differenced tree, discussed in more detail below, is returned to the parse requestor.

FIG. 3 depicts a block diagram of an exemplary process 200 for parsing binary data that includes initialization and runtime phases, where the runtime phase includes non-differencing and differencing parsing methods, as will be discussed in more detail below.

Process 200 starts with an initialization procedure where a value parser 205 initiates communication 210 with a parse definition file 215 to read the parse configuration. The value parser 205 uses this information to communicate with a value parser handler 225 and a data builder 265, with the objective being to create a parse tree 235 for parsing binary data 245. A value parser is a class of software that implements a data parsing algorithm for parsing binary data into data values. An exemplary parse definition file is in an XML schema, however, the parsing rules do not need to be expressed as XML schema but could be described in any manner known in the art. XML schema is a file format that describes the allowable elements, attributes, and values for an XML file, and may be used by a validating parser to verify the correctness of an XML input. XML schema allows for significantly greater control of the format of the XML data. In an exemplary embodiment, schema definitions are done in XML. The parse definition in definition file 215 is an XML that defines how to parse the binary input data stream. A value parser handler is a class of software that maps XML elements in a parse definition file to nodes in a parse tree.

The value parser 205 uses SAX, a simple application interface for XML that allows a program to interpret XML, to parse the parse definition in definition file 215 by sending 220 SAX callbacks to the value parser handler 225. Upon receipt of the SAX callbacks, the value parser handler 225 builds 230 a parse tree 235, which in general is a collection of nested parse nodes that define the format of the binary data to be read in, and once created, is stored in a memory by the value parser 205 and is used repeatedly for each parse method called. A parse node is an individual element in a parse tree and may be one of two types: primitive or container. Primitive parse nodes represent "primitive" values such as integers, strings, boolean strings, or any other native Java type of data, and are always "leaves" of the parse tree. Container nodes contain other parse nodes and are used for grouping, iterating and conditional switching, for example. The building of a parse tree is discussed in more detail below in reference to FIG. 4.

Once the complete XML parse definition is read in by the value parser 205, the parse tree 235 is ready to parse data.

The above process, steps 210, 220, 230, describe an initialization phase that creates a parse tree from the parse definition. The process that follows describes a runtime phase that uses the parse tree to parse the binary data received with a parse request.

At runtime, value parser 205 receives 240 binary data 245 and a parse request 250. Included in the parse request 250 is a call for either non-differenced parsing or differenced parsing, which will be discussed in more detail below, however, in general, non-differenced parsing returns a complete (updated) data tree of information to the parse requestor at 250, while differenced parsing returns a differenced tree only the information that has changed since the last known data set was saved.

Upon receipt 240 of binary data 245 and a parse request 250, the value parser 205 invokes 255 the parse tree 235, created in accordance with the discussion above, to parse the binary data 245.

Parsing of the binary data 245 at the parse tree 235 is performed in accordance with the received parse definition 215 and begins at the root of the parse tree. The receipt of the parse request 250 initiates a recursive set of calls, with each related parse node in the parse tree 235 calling a parse request on all of its children until a primitive parse node is found. When a primitive parse node is found, a get-value method is called to define and parse the value from the current position in the data stream for assignment to that parse node.

For each element read out of the data stream, the parse tree 235 calls 260 an insert-value method at the data builder 265, which in turn builds 270 a data tree 275 by managing and inserting the parsed value into the data tree 275. An element of the parse definition describes a given piece of data in the binary stream within the parse tree, while a value is the numerical value that results after the processing of the element. Callbacks from the value parser 205 are received at the data builder 265, via the value parser handler 225 and the parse tree 235, when a new piece of data has been parsed out of the binary data stream.

After all of the data has been read, the value parser 205 calls 280 the data tree 275 to allow it to perform any additional processing of its data before returning 285 the data tree 275 (one type of object returned to the parse requestor) back to the parse requestor at 250 where non-differenced parsing was originally called, or before calling 290 a differencing method where differenced parsing was originally called.

If differenced parsing was called, the value parser 205 will retrieve the last known data tree from its cache memory, stored previously when first created, and perform a comparative analysis between the last known data tree and the new (updated) data tree, passing 295 only the differences to a differenced tree 300 that will contain only that information that has changed since the last known data tree was saved.

After the creation of the differenced tree 300, the differenced tree 300 (another type of object returned to the parse requester) is returned 305 back to the caller of the parse at 250.

Figure 4:
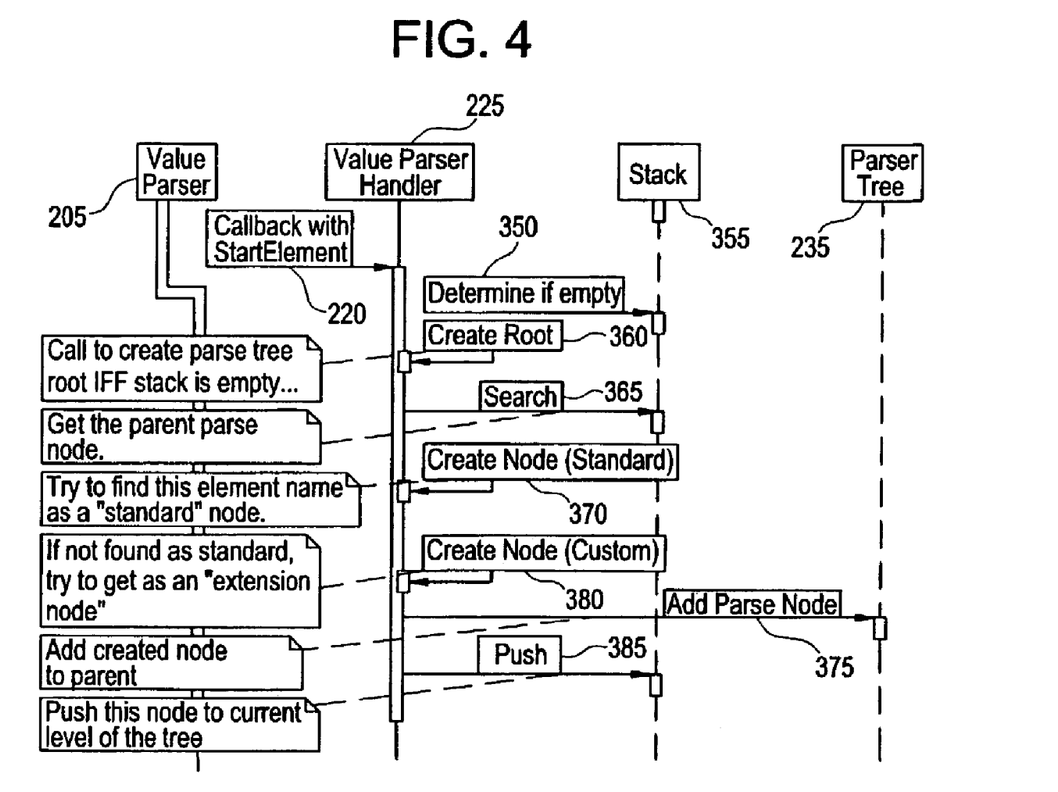
FIG. 4 is an exemplary process diagram for building a parse tree in accordance with an embodiment of the invention.

Referring now to FIG. 4, which depicts a process for building a parse tree 235, the value parser handler 225 builds the parse tree 235 after it has received a callback 220 from the value parser 205 that contains start and end elements within the binary data stream. The start and end elements of the parse definition describe the associated data in the data stream according to various parameters, such as for example, address, local name (the local name of an XML element is the name of the element minus any namespace considerations), qualified name and attributes for the start element, and address, local name and qualified name for the end element. Upon receipt of a parse request at the value parser 205, the value parser 205 parses the parse definition file 215 to read in the parse arguments and sends 220 a callback, containing the parse arguments, to the value parser handler 225.

The value parser handler 225 reads the XML element passed by the value parser 205 and if the element is a start-element, determines 350 whether the parse tree stack 355 is empty.

If the stack 355 is empty, the value parser handler 225 creates 360 a parse tree root node and pushes 385 the newly created node onto the parse tree 235. The parse tree root node is also referred to as a data tree root node and is the location in the tree where the value parser 205 will start the processing of the binary data 245.

If the stack 355 is not empty, the value parser handler 225 identifies the associated parent parse node by searching 365 the stack 355, and then attempts to match the XML element name to a set of known element names that are stored at the value parser 205 in a value parser tags file. Each known element name is then mapped at the value parser 205 to a specific parse tree node. If a matching element name is found, the value parser handler 225 creates 370 a standard parse tree node, adds 375 the standard node to the parse tree 235 starting at the parent parse node, maps the known element to the standard node, and pushes 385 the standard node to the current level of the parse tree 235. If a matching element name is not found, the value parser handler 225 creates 380 a custom parse tree node through a get-extension-node method, adds 375 the custom node to the parse tree 235 starting at the parent parse node, maps the non-matching element to the custom node, and pushes 385 the custom node to the current level of the parse tree 235.

The process of creating and adding nodes to the parse tree 235 continues until an end-element is encountered at the value parser 205. An end-element signifies completion of the parse tree for that particular binary data structure.

Figure 5:
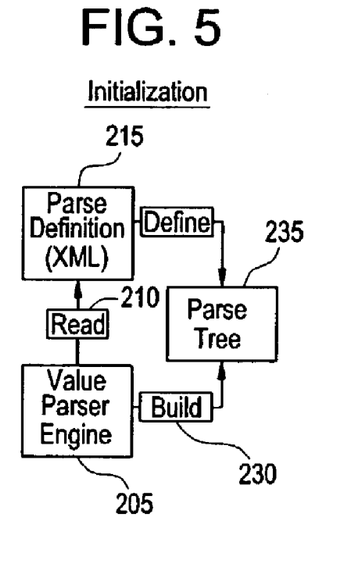
FIG. 5 is an exemplary block diagram of an initialization process in accordance with an embodiment of the invention.
Figure 6:
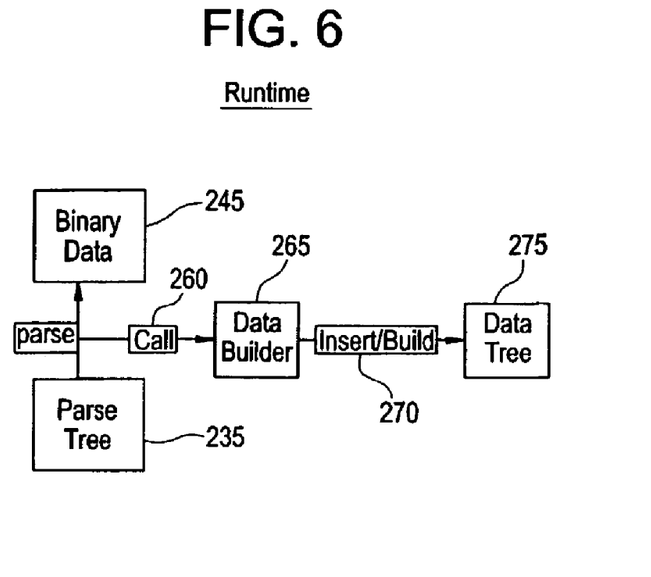
FIG. 6 is an exemplary block diagram of a runtime process in accordance with an embodiment of the invention.

From a more general viewpoint, and referring now to FIGS. 5 and 6, the value parser 205 is initialized by reading 210 an XML parse definition file 215 to build 230 a parse tree 235 representative of and defined by the parse definition. The parse definition file 215 specifies the format of the binary data 245 that will be accepted and processed by the value parser 205. At runtime, the parse tree 235 accepts binary data 245 containing primitive and non-primitive data elements. When a primitive data element is read from the binary stream, the parse tree 235 calls 260 the data builder 265 to insert 270 the data element into a data tree 275 at a primitive parse node. When a non-primitive data element is read from the binary stream, the parse tree 235 calls 260 the data builder 265 to insert 270 the data element into the data tree 275 at a non-primitive parse node. The data tree is a product of the value parser system, representing the binary data in a meaningful data structure. Applying differencing logic and conversion techniques, XML can further process this tree. The resulting data tree or differenced tree is returned to the parse requestor.

Figure 7:
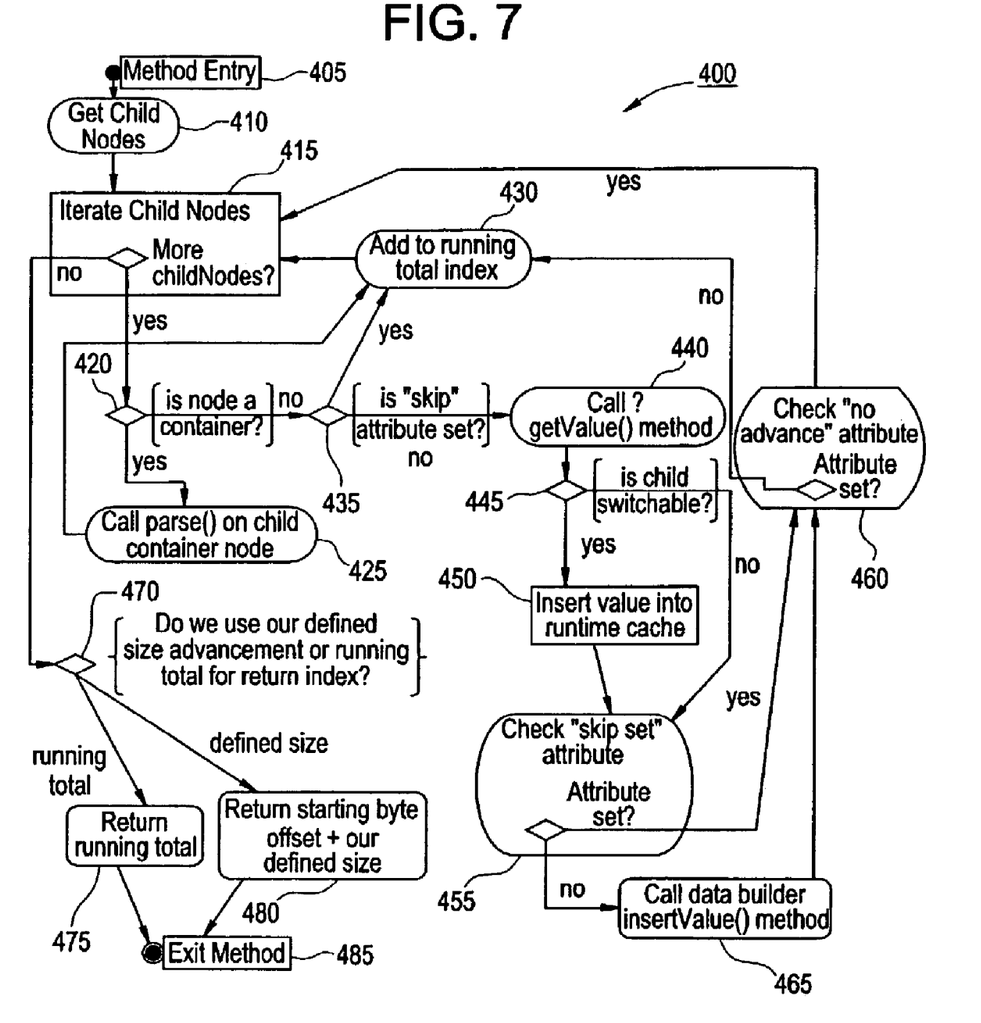
FIG. 7 is an exemplary process block diagram for parsing a parse tree node in accordance with an embodiment of the invention.

A detailed process 400 for parsing a parse tree node is depicted in FIG. 7, which begins at method entry 405 and proceeds to block 410 where child nodes are sought. At block 415, the child nodes are iterated if there are more child nodes present. If block 415 is true, it is determined 420 whether the node is a container node. If block 420 true, the child container node is parsed 425. After block 425, process logic passes to block 430 where a running total index of parsed nodes is updated. If block 420 is false, it is determined 435 whether a "skip" attribute to skip over binary data that is not to be interpreted is set. If block 435 is true, process logic passes to block 430. If block 435 is false, process logic passes to block 440 where the value of the child node is determined via a getValue algorithm. After block 440, process logic passes to block 445 where it is determined whether the child is switchable. A switchable node defines a value to be matched when it is switched on, that is, switchable is set to true. If switchable, the value of the node is temporarily stored in a memory for subsequent reference by a configuration file or data tree 275. If block 445 is true, the value from 440 is inserted 450 into a runtime cache. After block 450 or if block 445 is false, process logic passes to block 455 where it is determined whether the skip attribute is set. If block 455 is true, it is determined 460 whether the "no advance" attribute is set, which results in the read index not being advanced. For a given value read out of the data stream, the value is read, but the read pointer is not advanced. The no advance attribute is typically used with primitive elements inside of bitfield elements (i.e., a bitfield is a set of bytes that should be considered together) to prevent advancement of the read pointer. If block 455 is false, process logic passes to block 465 where data builder 265 is called to insert the value from block 440 into data tree 275.

If block 460 is true, process logic passes to block 415. If block 460 is false, process logic passes to block 430. After block 430, process logic passes to block 415. If block 415 is false, process logic passes to block 470 where the size of the return index is determined. If the running total is to be returned (where the "no advance" attribute is not set), then process logic passes to block 475 where the running total for the return index is returned. If the defined size advancement is to be returned (where the "no advance" attribute is set), then process logic passes to block 480 where the defined size for the return index is returned. After blocks 475 and 480, process logic passes to block 485 where process 400 exits.

An exemplary process for value parsing is described below using a simple example of processing a directory request response from trends. The process generally follows the process discussed above in reference to FIG. 3.

At the onset, the user identifies the binary format of the data 245 that needs to be parsed, and if the data 245 is sectional in nature, the user identifies the sections. Section identification is performed if the data always starts with a common header section or protocol identifier. For example, an ETFTP trend response always begins with a "Bed Message" structure (which is common most Unity I code), followed by an ETFTP request structure (which is common among code making ETFTP requests), followed by the trend data itself. These discrete sections are split into separate XML files and the master parse definition uses entity references to refer to them. An entity reference is a reference within an XML file that serves as a link to another XML file.

The user then identifies if the binary data format repeats or has a future section in the stream that depends on a prior read-in value. In this situation, the response format has three primary sections: a.a "ETFTPRequest" header (36 bytes) (see FIG. 9), which is a common section among all ETFTP requests, b.a "DataTrendMenu" block (7 bytes) (see FIG. 9), and c.a "TrendEntry" block (see FIG. 9), including a number of 6 byte entries, each representing a trend entry, which is a group category that serves to group elements together under a given name.

Figure 8:
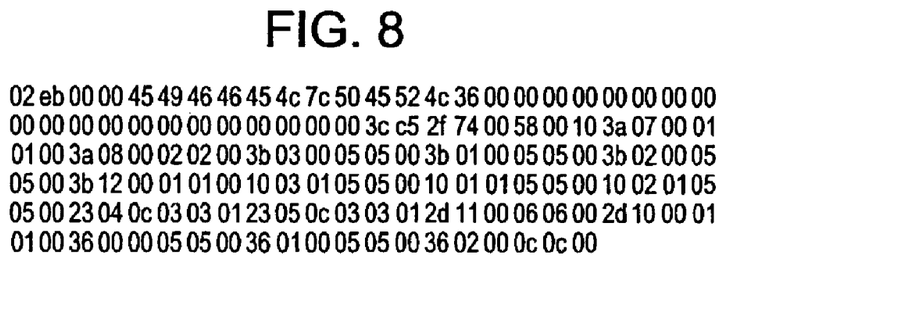
FIG. 8 is an exemplary illustration of a binary sequence for use in an embodiment of the invention.

An example of a binary trend directory response may look like the binary sequence depicted in FIG. 8.

Figure 9:
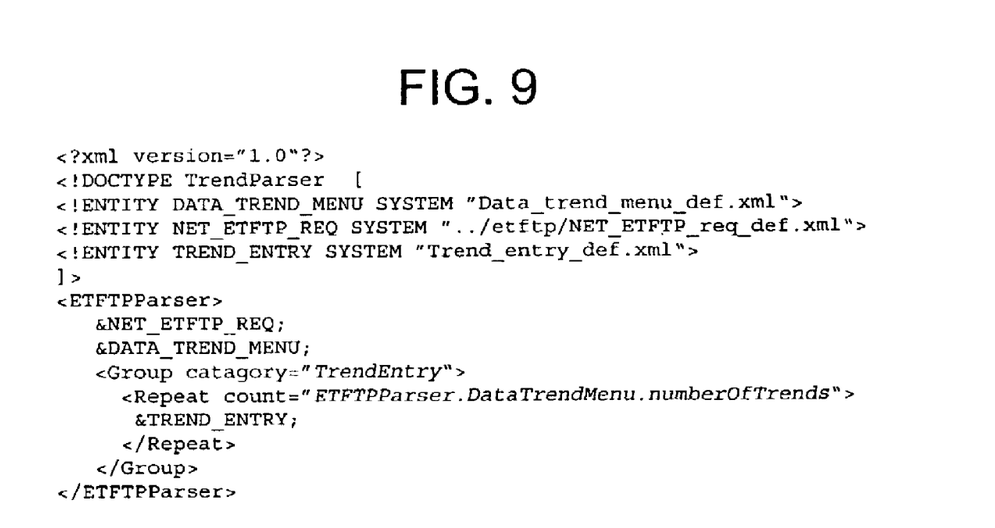
FIG. 9 is an exemplary XML parse definition file for use in an embodiment of the invention.
Figure 10:
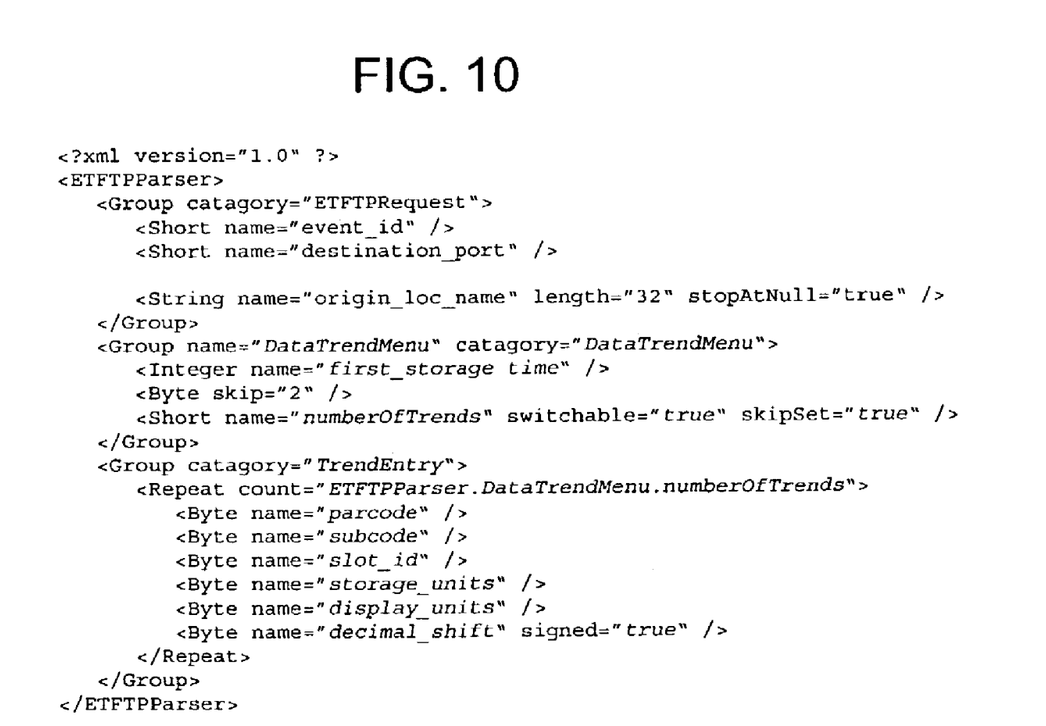
FIG. 10 is an exemplary resolved XML file for use in an embodiment of the invention.

Next, the user creates the parse definition file 215. Where the binary data is sectional, the parse definition file is defined into sections and external references are used to "glue" the sections together. The parse definition XML file is depicted in FIG. 9. In FIG. 9, the only value parser tags in the exemplary file are those specific to trend entries, and when the SAX parser reads in the file, the parser will resolve the entity references. The resolved XML file is depicted in FIG. 10. When all of the external references are resolved, which can be performed for viewing by dragging the XML file into a web browser (such as Internet Explorer™ 5.0 or higher), the parse definition is readable.

The user then creates a data builder 265, which receives callbacks from the parse tree 235 as it is processing the binary data 245. The data builder 265 builds a data tree 275 in whatever fashion the user wishes. This tree 275 can then be used to support differencing, passed as data to other methods, or converted to other formats (such as XML) for transmission. An exemplary data builder 265 for the exemplary binary stream of FIG. 8 is the "com.ge.med.rsvp.server.rsvpserver.unity.trend.TrendDirBuilder" class. The parse tree 235 will invoke an insert value 260 method on this class when a data value is read. The data builder 265 builds a "com.ge.med.rsvp.server.rsvpserver.trend.TrendDirectory" object as its data object (data tree 275).

At runtime, a data sink class calls value parser 205 when data 245 is received. A data sink is a class that receives data from a source such as a network or a file. The data sink class calls the value parser 205 to parse the retrieved data and forwards the data tree 275 to the requester. The data tree 275 returned is then passed to whoever needs it. A trend controller such as "com.ge.med.rsvp.server.rsvpserver.unity.trend.UnityTrendController", for example, calls a value parser 205 with the data received from its ETFTP request. The TrendDirectory object returned is passed as a result of the getDirectory process call.

It should be kept in mind that the binary stream format and parse tree syntax are free to change from the parsing algorithm, and since the binary stream is not hard coded, it can change with a new XML parse file. It is the structure and dynamic processing and not the actual input/output streams that are features of embodiments of the invention.

Using a parse definition file eliminates implementers of binary processing code from having to use long "case-type" statements to switch on data elements. Instead, the value parser system builds a parse tree for the data, which is called repeatedly for each binary data set received. Thus, the external processing code only needs to process the data tree from the parser. Since parse definitions are written in XML, entity references can be used to external XML files in order to piece together the whole definition, allowing common processing blocks to be shared among different parse definitions. This approach may be used in protocols where there are common headers followed by type specific information, and especially may be used for the parsing and distribution of medical binary data without having to embed protocol information into the system architecture. The use of a parse tree and a differenced tree for the transmission of medical binary data over communication lines, which may be low bandwidth lines, enables efficient encoding, compression and transmission of binary medical data.

Implementation of a parse definition file and parse tree also avoids the need to apply bit masks to the binary data or to use nested case statements in the code, which in turn avoids the need to recompile and redistribute software when the raw data is reinterpreted for different applications.

As described above, embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method for parsing binary data, comprising:
receiving binary data and a parse request at a value parser, the parse request calling for a differenced parsing method;
storing a last known data tree in a memory at the value parser;
invoking a parse free and receiving a parse definition to parse the received binary data;
parsing the binary data at the parse tree to define a value in accordance with the parse definition and calling a data builder to manage the value parsed;
inserting the value into an updated data tree;
retrieving the last known data tree from the memory at the value parser;
comparing the updated data tree to the last known data tree;
in response to the differenced parsing method being called, creating a differenced data tree that requires only the changes from the last known data tree be contained therein; and
in response to the differenced parsing method being called, returning the differenced data tree to the parse requestor;
wherein the differenced data tree provides for improved data transmission over existing communication lines, thereby eliminating the need for a line bandwidth upgrade.

2. The method of claim 1, further comprising:
initiating communication between a value parser and a parse definition file and parsing the parse definition file; and
building a parse tree at a value parser handler.

3. The method of claim 1, further comprising:
calling for a non-differenced parsing method; and
in response to the non-differenced parsing method being called, returning the updated data tree to the parse requestor.

4. The method of claim 2, wherein said building a parse tree comprises:
reading an element into the value parser handler and determining if a parse tree stack is empty;
creating a parse tree root if the stack is empty;
searching the stack for a matching known element name;
identifying a parent parse node, creating a standard node, adding the standard node to the parent parse node, and mapping the element to the standard node if the matching known element name is found;
identifying a parent parse node, creating a custom node, adding the custom node to the parent parse node, and mapping the element to the custom node if the matching known element name is not found.

5. The method of claim 1, wherein said parsing the binary data comprises:
parsing a root of the parse tree, the parse tree representing the structure of the binary data;
parsing a child of each parse node stemming from the root until a primitive parse node is identified;
defining and parsing a value at the current position in the binary data for association with the primitive parse node; and
calling a data builder to insert the parsed value into a data tree.

6. A method for parsing medical binary data for transmission over a communication line, comprising:
receiving binary data and a parse request at a value parser, the parse request calling for at least one of a non-differenced parsing method or a differenced parsing method;
storing a last known data tree in a memory at the value parser;
invoking a parse tree and receiving a parse definition to parse the received binary data;
parsing the binary data at the parse tree to define a value in accordance with the parse definition and calling a data builder to manage the value parsed;
inserting the value into an updated data tree;
in response to the differenced parsing method being called, retrieving the last known data tree from the memory at the value parser;
in response to the differenced parsing method being called, comparing the updated data tree to the last known data tree;
in response to the differenced parsing method being called, creating a differenced data tree that requires only the changes from the last known data tree be contained therein; and
returning at least one of the updated data tree or the differenced data tree to the parse requestor;
wherein the at least one of the updated data tree or the differenced data tree provides for improved data transmission over existing communication lines, thereby eliminating the need for a line bandwidth upgrade.

7. The method of claim 6, wherein:
said inserting the value further comprises inserting the value into an updated data tree having an absence of embedded protocol information; and
said creating a differenced tree further comprises creating a differenced data tree having an absence of embedded protocol information.

8. A system for parsing binary data, comprising:
a hospital computer system in communication with a network, said hospital computer system including software to implement a method for parsing medical binary data for transmission over a communication line, said method comprising:
receiving binary data and a parse request at a value parser, the parse request calling for at least one of a non-differenced parsing method or a differenced parsing method;
storing a last known data tree in a memory at the value parser;
invoking a parse tree and receiving a parse definition to parse the received binary data;
parsing the binary data at the parse tree to define a value in accordance With the parse definition and calling a data builder to manage the value parsed;

inserting the value into an updated data tree;
retrieving the last known data tree from the memory at the value parser if the differenced parsing method was called;
comparing the updated data tree to the last known data tree if the differenced parsing method was called;
creating a differenced data tree that requires only the changes from the last known data tree be contained therein if the differenced parsing method was called; and
returning at least one of the updated data tree or the differenced data tree to the parse requestor.

9. The system of claim 8, further comprising:
a network, and said hospital computer system being in communication with said network.

10. The system of claim 9, wherein said network is an internet.

11. The system of claim 9, wherein said network is an Intranet.

12. The system of claim 9, wherein said network is wireless.

13. The system of claim 8, wherein:
said inserting the value further comprises inserting the value into an updated data tree having an absence of embedded protocol information; and
said creating a differenced data tree further comprises creating a the differenced data tree having an absence of embedded protocol information.

14. The system of claim 13, further comprising:
a network, and
said hospital computer system being in communication with said network.

15. The system of claim 14, wherein said network is an internet.

16. The system of claim 14, wherein said network is an intranet.

17. The system of claim 14, wherein said network is wireless.

18. A method for parsing binary data, comprising:
initializing a value parser by reading a parse definition file and creating a parse tree representative of the parse definition;
accepting binary data input having at least one of a primitive data element or a non-primitive data element at the value parser and the parse tree;
calling a data builder in response to the primitive data element and inserting the primitive data element into an updated data tree at a primitive parse node;
calling a data builder in response to the non-primitive data element and inserting the non-primitive data element into the updated data tree at a non-primitive parse node; and
establishing and returning at least one of the updated data tree or a differenced data tree that requires only the changes from a last known data tree be contained therein;
wherein the at least one of the undated data tree or the differenced data tree provides for improved data transmission over existing communication lines, thereby eliminating the need for a line bandwidth upgrade.

19. The method of claim 18, wherein said establishing and returning at least one of the updated data tree or a differenced data tree comprises:
comparing the updated data tree with a cached last known data tree;
creating a differenced data tree; and
returning the differenced data tree.

20. The method of claim 19, wherein said returning the differenced data tree comprises:
returning the differenced date tree in the absence of embedded protocol information.

21. A computer program product for parsing binary data, the product comprising:
a storage medium, readable by a processing circuit, storing instructions for execution by the processing circuit for:
receiving binary data and a parse request at a value parser, the parse request calling for at least one of a non-differenced parsing method or a differenced parsing method;
storing a last known data tree in a memory at the value parser;
invoking a parse tree and receiving a parse definition to parse the received binary data;
parsing the binary data at the parse tree to define a value in accordance with the parse definition and calling a data builder to manage the value parsed;
inserting the value into an updated data tree;
in response to the differenced parsing method being called, retrieving the last known data tree from the memory at the value parser;
in response to the differenced parsing method being called, comparing the updated data tree to the last known data tree;
in response to the differenced parsing method being called, creating a differenced data tree that requires only the changes from the last known data tree be contained therein; and
returning at least one of the updated data tree or the differenced data tree to the parse requestor.

22. The computer program of claim 21, wherein:
said inserting the value further comprises inserting the value into an updated data tree having an absence of embedded protocol information; and
said creating a differenced data tree further comprises creating a differenced data tree having an absence of embedded protocol information.

23. The method of claim 21, wherein said instructions are XML instructions.

* * * * *

UNITED STATES PATENT AND TRADEMARK OFFICE
CERTIFICATE OF CORRECTION

PATENT NO. : 7,111,286 B2  Page 1 of 1
APPLICATION NO. : 10/248097
DATED : September 19, 2006
INVENTOR(S) : Stuart Lyle Schrader et al.

It is certified that error appears in the above-identified patent and that said Letters Patent is hereby corrected as shown below:

Column 11,
Line 24, after "parse" delete "free" and insert therefor -- tree --.

Column 12,
Line 66, after "accordance" delete "With" and insert therefor -- with --.

Column 13,
Line 19, after "an" delete "Intranet" and insert therefor -- intranet --.

Signed and Sealed this

Thirtieth Day of January, 2007

JON W. DUDAS
*Director of the United States Patent and Trademark Office*